United States Patent
Rojas et al.

(10) Patent No.: US 6,916,469 B2
(45) Date of Patent: Jul. 12, 2005

(54) GELLABLE ANT BAIT MATRIX

(75) Inventors: Maria Guadalupe Rojas, Metairie, LA (US); Juan A. Morales-Ramos, Metairie, LA (US); Ligia M. Hernandez, Kenner, LA (US); Jonathan D. Peters, Independence, LA (US)

(73) Assignees: The United States of America as represented by the Secretary of Agriculture, Washington, DC (US); Waterbury Companies, Inc., Waterbury, CT (US)

( * ) Notice: Subject to any disclaimer, the term of this patent is extended or adjusted under 35 U.S.C. 154(b) by 111 days.

(21) Appl. No.: 10/370,954

(22) Filed: Feb. 20, 2003

(65) Prior Publication Data

US 2004/0166138 A1 Aug. 26, 2004

(51) Int. Cl.$^7$ ................................. A01N 25/04
(52) U.S. Cl. ................ 424/84; 424/406; 424/410
(58) Field of Search ................ 424/84, 405–410, 424/417, 421

(56) References Cited

U.S. PATENT DOCUMENTS

| 5,152,096 A | * | 10/1992 | Rudolph ...................... 43/131 |
| 5,939,061 A | * | 8/1999 | Vail et al. ...................... 424/84 |
| 2004/0057976 A1 | * | 3/2004 | Warner et al. .............. 424/410 |

FOREIGN PATENT DOCUMENTS

| EP | 000431468 A1 | * | 6/1991 |
| WO | 00/62610 | * | 10/2000 |

* cited by examiner

*Primary Examiner*—Neil Levy
(74) *Attorney, Agent, or Firm*—John D. Fado; Curtis P. Ribando; Lesley Shaw

(57) ABSTRACT

Ant foods mixed together in a matrix suitable to be used as baits for ants are provided. This ant matrix is preferred by ants over naturally-occurring foods such as other known ant matrices. It comprises protein, carbohydrate, fat and sterol as ant-preferred nutrients and uric acid as a bait enhancing agent is carried in a unique gel system that is specifically attractive to insects. Methods of controlling ants using such matrices to deliver ant toxins are also provided.

4 Claims, No Drawings

GELLABLE ANT BAIT MATRIX

BACKGROUND OF THE INVENTION

This invention relates to a nutritionally based baiting composition and methods for its use in the control of ants of multiple species.

Damage in the United States attributable to the Red Imported Fire Ant (*Solenopsis invicta*) is now estimated to be in millions of dollars a year. Since its arrival into the United States at Mobile, Ala. around 1920 the fire ant has spread widely across the southern United States and can be found in 17 states and Puerto Rico and northern Mexico. The ants cause problems to urban, agricultural and wildlife areas. Since their introduction to the United States, fire ants (*Solenopsis invicta*), have become one of the most destructive pests in the contiguous United States. Reasons for this include their numerous 1–1.5 foot tall colonies which can contain 200,000 to 300,000 individuals, at a density of up to 30 to an acre (Vinson, S. B., 1997, Invasion of the Red Imported Fire Ant (hymenoptera: Formicidae), Am. Entomol. 23–29). The fire ant is a highly aggressive stinger and humans when stung develop a pustule at the sting site.

The most successful methods for control of fire ants involve dissolution of the active agent in refined soybean meal mixed with corn grit. Patented baiting systems involve the use of powdered dry pet food (Purina Dog Chow) mixed with the active agent are taught by Erwin (U.S. Pat. No. 5,575,996 dated Nov. 19, 1996). Vail et al. (U.S. Pat. No. 5,939,061 dated Aug. 17, 1999) teaches the use of sugar, salt and water as a base for toxic constituents for use against fire ants.

Stein et al. in Seasonal Changes in Bait Preference by the Red Imported Fire Ant, *Solenopsis invicta* (Hymenoptera: Formicidae) Florida Entomologist, 73:117–123 (1997) disclose that foragers were more attracted to carbohydrate baits during sampling periods registering lower temperatures (mean=17° C.) and were more attracted to proteinaceous baits when the seasonal temperatures were greater (mean=25° C.). Glunn et al. (Food Preference in Colonies of the Fire Ant *Solenopsis Invicta, Insectes Sociaux*, Paris 1981, Volume 28, No. 2, pp. 217–222) teach that there was heterogeneity among the 10 colonies tested of preference patterns. Among these ten colonies there were seven different preference hierarchies. Lanza et al. (Preferences of the Fire Ants *Solenopsis invicta* and *S. geminata* (Hymenoptera: Formicidae) for Amino Acid and Sugar Components of Extrafloral Nectars; Environmental Entomology, Vol. 22, No. 2, pp. 411–417) show that both insect species are attracted to amino acid content and sugar content in plants and that differences in recruitment cannot be accurately predicted based on simple assumptions of nutrient maximization or energy content. Williams et al. (Fly Pupae as Attractant Carriers for Toxic Baits for Red Imported Fire Ants (Hymenoptera: Formicidae), Journal of Economic Entomology, Vol. 83, No. 1, pp. 67–73) disclose the potential of using fly pupae and eye gnat pupae as carrier system for fire ant baits that eye gnats might represent less of a target to be fed upon by other animals such as birds.

Carpenter ants (*Camponotus modoc*) are common in wooden areas and will infest structures in the United States. *Camponotus* comprises the ant species that will cause the greatest damage to wooden buildings. During the spring when the larvae are growing foraging for proteinaceous foods dominate, they switch to primarily carbohydrate based foods for the summer. Late summer and onwards they switch back to primarily proteinaceous foods. They consume large amounts of food in the autumn in preparation for the winter.

Argentine ants (*Linepithema humile*) are a common ant throughout the southeastern United States and are a cause of significant structural damage in California. This ant is very competitive and can out-compete the fire ant. This ant is capable of causing damage to citrus trees by protecting aphids, mealybugs and scale insects from their natural predators.

While various methodologies and compositions exist for the control of ants, there remains a need for the creation of improved tools in this area.

Therefore, it is an object of this invention to provide a gellable bait matrix composition effective as a toxicant delivery system for ants including fire ants.

Another object is to provide compositions and methods for the effective control of ant and fire ant populations.

SUMMARY OF THE INVENTION

We have discovered that ants and fire ants may be more effectively controlled through use of a gellable nutritionally-based matrix which works as an attractant and carrier for chemicals which are toxic to ants and fire ants. A fire ant matrix containing nutritionally requisite components enhances its usefulness as a bait. The fire ant matrix of this invention is preferred by fire ants over other bait systems presently available. A difficulty in fire ant control is that their nutrition and feeding preferences change seasonally. The objective was to develop a bait matrix that maximized consumption by ants year-round. Its gellable formulation contains one or more pectins or plant derived polysaccharides, a calcium salt and a toxicant. The pectin is a purified carbohydrate product obtained by aqueous extraction of plant material, usually citrus fruits or apples. Pectin is an essentially linear polysaccharide containing from a couple hundred to about 1,000 saccharide units in a linked configuration. The bait also includes an ant attractant and simulates the chemical composition of the main ant foods, such as: seeds, nectar and insects. This ant attractant comprises a cellulose, a sugar component, a plant starch, an instant nonfat dry milk, dried egg yolk, a sterol compound, uric acid and a plant based oil.

The gellable matrix offers the benefit of the ability to apply the bait in cracks and areas not normally available to ant baiting systems. The present bait system is unique in its requirement for approximately balanced concentrations in the form of proportions of protein, carbohydrate and fat. This allows the composition to be acceptable year round for ants. The standard formulations available do not have this balance and have seasonal fluctuations in their acceptability by ant populations. The present bait is also unique in its requirement that the bait contain uric acid, which serves to make the bait more attractive to the ants. It is the belief of the inventors that this material alters the perception of the ant to make them believe the food material is of insect origin, and thereby more acceptable for consumption. Uric acid is by far the most nitrogenous constituent in the urine of insects. Uric acid is present in the malphagian tubules, the equivalent to vertebrate kidneys, branching from the hindgut and spreading inside the insect body cavity (V. B. Wigglesworth, The Principles of Insect Physiology, Seventh Edition).

In addition the gellable matrix contains ant-preferred nutrients, i.e., nutrients required for ant growth and development. These nutrients are selected and present in the ant matrix of this invention in such amounts that the ant matrix is preferred by ants over alternate available food sources such as sugar, corn grits and oil used in ant baits known to the art.

Ants for which the ant matrix of this invention is useful include all ant species belonging to the family Formicidae, preferably the red imported fire ant (*Solenopsis invicta*), black imported fire ant (*Solenopsis richteri*), native fire ant (*Solenopsis germinata*), southern fire ant (*Solenopsis xyloni*), carpenter ant (*Camponotus modoc*), argentine ant (*Linepithema humile*), pharaoh ants (*Monomorium pharaonis*), whitefooted ants (*Technomyrex albipes*), little black ants (*Monomorium minimum*), ghost ants (*Tapinoma melanocephalum*), odorous house ant (*Tapinoma sessile*) and pavement ants (*Tetramorium caespitum*).

The matrix may be used as a highly effective carrier for enhancing the delivery of toxins for the purpose of destroying substantial numbers of ants and thus inhibiting ant damage.

Methods of making ant-preferred matrices of this invention are also provided comprising mixing the various components to form a food, and preferably including the steps of separately mixing autoclavable components, autoclaving, and adding components which do not tolerate heat to such. The method need not include heat sterilization but preferably does, since constituents may contain fungal spores which can make the matrix less attractive. The method also includes adding ant toxins to the gellable bait formulation of the matrix.

Methods of killing ants are also provided comprising placing a toxin-containing matrix in a termite habitat upon which the ants will preferentially feed in place of other environmentally-available food sources.

DETAILED DESCRIPTION

A bait matrix composition for ants has been developed which sufficiently fulfills the nutritional needs of the red imported fire ant so as to be preferred by ants. The gel matrix comprises an aqueous combination of one or more pectin or similar plant derived polysaccharides, and a calcium salt. This matrix further contains an ant attractant comprising: cellulose, a sugar, a plant starch, an instant nonfat dry milk, dry egg yolk, a sterol compound, uric acid, an oil and one or more toxicants.

The pectin or plant derived polysaccharide is selected from one or more of the group consisting of pectin, guar gum, locust bean gum, karaya gum, xanthan gum and tragacanth gum. This component is present in the bait composition in a weight ratio ranging from about 2% to about 5%. The calcium salt is selected from one or more of the group consisting of calcium chloride, calcium propionate, and calcium carbonate. This component is present in the bait composition in a weight ratio ranging from about 0.01% to about 0.5% by weight.

The toxicant can be selected from any known ant toxicant but preferably includes but is not limited to boric acid, Fipronil, Hexaflumoron, Hydramethylnon, Diflubenzuron, Sulfuramid, Avermectin, Abamectin and a pyrethroid compound such as Deltamethrin. This component is present in the gellable carrier system in a weight ratio ranging from about 0.001% to about 10% by weight.

The dry ant attractant is present in the bait composition in a weight ratio ranging from about 20% to about 40% by weight. The water component of the composition is present in the bait composition in a weight ratio ranging from about 40% to about 70% by weight.

The dry ant attractant component of the bait is comprised of several ingredients which is set forth as follows:

The cellulose may be supplied by means of any cellulose-containing material, preferably having 90% to greater than 95% cellulose, so long as it does not include chemicals which are toxic or repellant to ants. Such materials include commercially available cellulose, wood, paper, and cardboard, and are preferably in particulate form for ease of mixing with the other ingredients of the matrix. Alternate sources of sawdust, such as lumber mill sawdust and sugar cane bagasse while usable, may contain chemicals in amounts that reduce the utility of such sawdust materials due to either repellant or toxic effects. Preferably, commercially available cellulose powder is used because it is less expensive than sawdust and lacks such chemicals. This component is present in the dry ant attractant in a weight ratio ranging from about 0.01% to about 10% by weight.

The sugar component is selected from sources such as sucrose, arabinose, xylose, glucose, trehalose, fructose, lactose, maltose and glucosamine. Sources such as molasses, honey, and brown sugar are acceptable. This component is present in the dry ant attractant in a weight ratio ranging from about 1% to about 10% by weight.

The plant starch is selected from any plant source such as corn starch, potato starch, wheat starch and rice starch. This component is present in the dry ant attractant in a weight ratio ranging from about 0.5% to about 5% by weight.

The instant nonfat dry milk can be prepared from any source, this component is present in the dry ant attractant in a weight ratio ranging from about 30% to about 60% by weight.

The dried egg yolk is from any egg source such as a chicken, duck or turkey. This component is present in the dry ant attractant in a weight ratio ranging from about 20% to about 60% by weight.

The sterol compound is selected from ergosterol or cholesterol. This component is present in the dry ant attractant in a weight ratio ranging from about 0.0001% to about 0.010% by weight.

The uric acid compound is present in the dry ant attractant in a weight ratio ranging from about 0.1% to about 1% by weight.

The oil component is selected from any known plant oil or combination including: corn, sunflower, soybean, canola, cottonseed, safflower, meadowfoam, cuphea, sesame, peanut, tung and olive that is not disruptive to uptake by the ants. This component is present in the dry ant attractant in a weight ratio ranging from about 2% to about 15% by weight.

An ant attractant formulated as described above will preferably contain about 20%–40% protein, about 20%–40% fat and about 20%–40% carbohydrate in the dry state. Water is added to provide a final concentration by weight of about 40% to about 70%.

EXAMPLES

TABLE 1

Ant Bait Formulation
Ant bait formulation (dry)

| Chemical | Amount in g | Percent | Manufacturer | Product Number |
|---|---|---|---|---|
| Cellulose | 16.0 | 2.7 | Bioserv | 3425 |
| Pure Grain Sugar | 24.0 | 4.0 | Save-A-Center | |
| Corn Starch | 8.0 | 1.3 | Save-A-Center | Argo |
| Instant Nonfat | | | | |

TABLE 1-continued

Ant Bait Formulation
Ant bait formulation (dry)

| Chemical | Amount in g | Percent | Manufacturer | Product Number |
|---|---|---|---|---|
| Dry Milk | 247.0 | 41.6 | Save-A-Center | |
| Dry Egg Yolk | 240.0 | 40.5 | Sigma 02' | E-0625 |
| Ergosterol | 0.02 | 0.003 | Sigma | E-6510 |
| Uric Acid | 3.0 | 0.5 | Sigma | U-2625 |
| Pure Canola Oil | 50.0 | 8.4 | Save-A-Center | Wessen |
| Cottonseed Oil | 6.0 | 1.0 | Sigma | C-7767 |
| Spring Water | 480.0 | | Sigma | C-7767 |
| TOTAL DRY WT. | 594.02 | 100.003 | | |

The formulation of Table 1 is made as follows:

The canola oil, cotton oil and ergosterol was mixed in a 250 ml glass beaker. A teflon coated stirring bar was added and stirred using a stirring plate until the material was completely mixed. The rest of the ingredients were weighed out and put into a stainless steel bowl and mixed to get a lump free paste. The rest of the oil mixture was added, with continued mixing until the paste is homogenous, then was spread the paste on a cookie sheet covered with aluminum foil. The cookie sheet and mixture was placed in a vacuum oven set at 60° C. and dry vacuum at 20 psi until dryness. The ant bait is then ground until the particles are about 1 mm or less in diameter.

TABLE 2

Bait matrix composition

| | Amount for 100 g | Manufacturer | Product |
|---|---|---|---|
| Spring Water | 55.0 | Robert's | Barbe's |
| Calcium Chloride | 0.1 | Sigma 02' | C-5426 |
| Pectin | 3.0 | Sigma 02' | P-8471 |
| Ant Bait Formulation | 33.17 | Mix Table 1 | Dried or Powder |
| Canola Oil | 3.2 | Save-A-Center | Wessen |
| Xanthan Gum | 0.5 | Sigma 02' | G-1253 |
| Boric Acid | 5.0 | US Borax | MG Powder |
| Yeast | 0.03 | ICN Biologicas | 103304 |
| TOTAL AMOUNT | 100.0 | | |

The gel bait matrix composition of Table 2 was prepared by weighing the canola oil, and non-water soluble toxicants into a weighing boat and mixing it well using a stainless steel paddle.

Water and calcium chloride were weighed into a 250 ml glass beaker containing a thermometer. The beaker was placed on top of a heating plate until the water reached a temperature of 96° C. To prevent evaporation, the opening of the beaker was covered with foil. Once the water reached the desired temperature, the rest of the chemicals were sequentially added, under constant stirring with an electric mixer starting with the boric acid, followed by the combined mixture of the pectin and ant attractant, canola oil and gums. Care was taken so chemicals were homogeneously blended into the mixture and became lump free. If non-water soluble ingredients were used, then the active agent was previously mixed with the oil to maintain the 100 gram constant, the amount of water and ant attractant were equally reduced according to the amount of active ingredient added.

While the preferred embodiments have been described above, it will be recognized and understood that various modifications may be made in the invention and the appended claims are intended to cover all such modifications which may fall in the spirit and scope of the invention.

We claim:

1. A gelatinous bait matrix for attracting and killing ants comprising:

a.) water in an amount of 40–70% by weight, b.) a salt selected from the group consisting of calcium chloride, calcium propionate and calcium carbonate in an amount of 0.01–0.5% by weight, c.) pectin or plant derived polysaccharide in an amount of 30–40% by weight, d.) a toxicant effective against ants in an amount of about 0.0001% to about 6% by weight, and e.) an ant attractant in an amount of 20–40% by weight, wherein said attractant comprises:

i.) a cellulose,
ii.) a sugar,
iii.) a plant starch,
iv.) an instant nonfat dry milk,
v.) a dried egg yolk,
vi.) a sterol compound,
vii.) uric acid, and
viii.) a plant based oil.

2. The gelatinous bait matrix for attracting and killing ants of claim 1 wherein the uric acid is present in a concentration of 0.1% to about 1% by weight of ant attractant.

3. A gelatinous bait matrix for attracting and killing ants comprising:

| | | |
|---|---|---|
| a.) | spring water | about 55.0% by weight, |
| b.) | calcium chloride | about 0.1% by weight, |
| c.) | pectin | about 3.0% by weight, |
| d.) | xanthan gum | about 0.5% by weight, |
| e.) | boric acid | about 5.0% by weight, and |
| f.) | ant bait formulation | about 38.9% by weight |
| | said formulation comprising: | |
| i.) | cellulose | about 2.6% by weight, |
| ii.) | pure grain sugar | about 3.8% by weight, |
| iii.) | corn starch | about 1.3% by weight, |
| iv.) | instant nonfat dry milk | about 44.6% by weight, |
| v.) | dry egg yolk | about 39.0% by weight, |
| vi.) | ergosterol | about 0.003% by weight, |
| vii.) | uric acid | about 0.5% by weight, and |
| viii.) | canola oil | about 3.2% by weight. |

4. A gelatinous bait matrix for attracting and killing ants comprising:

a.) water in an amount of 40%–70% by weight, b.) a salt selected from the group consisting of calcium chloride, calcium propionate and calcium carbonate in a concentration of 0.01% to 0.5% by weight, c.) pectin or plant derived polysaccharide in a concentration of 30% to 40% by weight, d.) a toxicant effective against ants in a concentration of about 0.0001% to about 6% by weight, and e.) an ant attractant in a concentration of 20% to 40% by weight, wherein said attractant comprises:

i.) a cellulose in a concentration of 1% to 5% by weight of attractant, ii.) a sugar component in a concentration of 1% to 10% by weight of attractant, iii.) a plant starch component in a concentration of 0.5% to 5% by weight of attractant, iv.) an instant nonfat dry milk in a concentration of 30% to 60% by weight of attractant,
v.) a dried egg yolk in a concentration of 20% to 60% by weight of attractant,
vi.) a sterol compound in a concentration of 0.0001% to 0.01% by weight of attractant,
vii.) uric acid in a concentration of 0.1% to about 1% by weight of attractant, and
viii.) a plant based oil in a concentration of 2% to 15% by weight of attractant.

* * * * *